United States Patent [19]

Wangersky et al.

[11] Patent Number: 5,057,432
[45] Date of Patent: Oct. 15, 1991

[54] CAGE-CULTURE TURBIDOSTAT

[76] Inventors: Peter J. Wangersky, 6071 South Street, Halifax, Nova Scotia, Canada, B3H 1S9; Charles P. Wangersky, 812 Young Avenue, Halifax, Nova Scotia, Canada, B3H 2V7

[21] Appl. No.: 469,726

[22] Filed: Jan. 24, 1990

Related U.S. Application Data

[63] Continuation of Ser. No. 826,267, Feb. 5, 1986, abandoned.

[51] Int. Cl.⁵ .................. C12M 1/34; C12M 1/36; C12M 1/40
[52] U.S. Cl. .................. 435/289; 210/333.01; 210/321.69; 210/411; 422/101; 422/105; 422/108; 422/110; 422/111; 422/82.09; 435/288; 435/291; 435/311
[58] Field of Search .................. 422/110–111, 422/108, 105, 68, 101; 435/288–289, 291, 311, DIG. 808; 210/333.01, 411, 321.69

[56] References Cited

U.S. PATENT DOCUMENTS

| | | | |
|---|---|---|---|
| 2,970,696 | 2/1961 | Mummert | 210/411 X |
| 2,990,339 | 6/1961 | Frank et al. | 435/289 |
| 3,195,726 | 7/1965 | Saurenman et al. | 210/411 X |
| 3,363,765 | 1/1968 | Rowe | 210/411 X |
| 3,954,621 | 5/1976 | Etani et al. | 210/333.01 X |
| 4,073,691 | 2/1978 | Anhell et al. | 435/311 X |
| 4,411,792 | 10/1983 | Babb | 210/411 X |
| 4,636,473 | 1/1987 | Kleinstreuer | 435/289 |
| 4,686,189 | 8/1987 | Redikultsev et al. | 435/289 |

OTHER PUBLICATIONS

Shelef et al. (1971), Proceedings Eighth International Conference Water Pollution Resource, Paper No. 3-25.
Sakshaug et al. (1978), *Oceanogr. Mar. Biol. Ann. Rev.*, 16, pp. 81–106.
Premazzi et al. (1987), *Mitt. Internatl. Verein. Limnol.*, 21, pp. 42–49.
Sorgeloos et al. (1976), *Applied and Environmental Microbiology*, 31, pp. 327–331.
Watson (1972), *J. Appl. Chem. Biotechnol.*, 22, pp. 229–243.
Skipnes et al., "Cage Culture Turbidostat: A Device for Rapid Determination of Algal Growth Rate", *Applied and Environmental Microbiology*, Aug. 1980, pp. 318–325.
Zhou et al. (1985), *Marine Chemistry*, 17, pp. 301–312.

*Primary Examiner*—Robert J. Warden
*Assistant Examiner*—Amalia L. Santiago
*Attorney, Agent, or Firm*—Banner, Birch, McKie & Beckett

[57] ABSTRACT

A cage-culture turbidostat as described for growing organisms at a constant population density which avoids the problem of filters clogging and nutrient dilution and facilitates the analysis of the growth and development of the organisms. The cage-culture turbidostat minimizes reintroduction of spent nutrient medium through the filters during backwashing.

4 Claims, 3 Drawing Sheets

CAGE-CULTURE TURBIDOSTAT

This application is a continuation of application Ser. No. 826,267, filed Feb. 5, 1986 now abandoned.

BACKGROUND OF THE INVENTION

1. Field of the Invention

This invention relates to an apparatus for examining the response of an organism to changes in its environment. This invention particularly pertains to improvements in cage-culture turbidostat design and operation for culturing organisms and cells at a constant population density.

2. Description of Related Art

A cage-culture turbidostat is a device useful, for example, for examining both the chronic toxicity and the acute toxicity of various substances to a particular microorganism or cell. In a cage-culture turbidostat a colony of microorganisms or cells is grown in an isolated vessel or growth chamber as a suspension culture at a constant population density. The culture is kept in suspension in the growth chamber by a mechanical or magnetic stirrer. The turbidity of the culture suspension normally is used as an indication of the cellular population. A photo-sensitive detector measures the magnitude of a signal transmitted through a representative portion of the culture vessel from a light source. In the case where light must be provided for the growth of the organisms, the same light source can also be used to monitor and regulate turbidity. When the strength of the received signals falls below some pre-set value, indicating an increase in the cell density in the culture vessel, a control circuit is energized and a portion of the biomass is removed from the culture vessel, for example, by simply opening a drain valve or by pumping. As soon as such harvesting has lowered the cell population in the culture vessel to a point where the strength of the received light signal increases above a second pre-set value, the control circuit terminates the remedial harvesting action.

Thus, by measuring variations in the turbidity of the culture suspension, using one or more photo-sensitive detectors, the quantity of growing cells in the culture vessel can be automatically controlled. The growth rate of the cells or microorganisms under investigation then can readily be determined from the operating time of the harvesting or dilution system, which normally is integrated over some convenient time period.

In the standard design, the growth chamber of the culture vessel is isolated or confined by spaced screens, filters or porous membranes, hereinafter referred to as filters. The particular filters used depend, inter alia, upon the size of the cell or organism being studied. The filters are designed to allow substantially unrestricted passage of fresh and spent nutrient medium into and out of the growth chamber respectively, but to prevent any loss of the cultured cells or organisms and the ingress of unwanted cells and organisms. Such design allows one to independently vary the flow rate of the nutrient medium and the density of cells in the growth chamber while avoiding the problem of wash-out often encountered in chemostats. Thus, this device provides a powerful analytical tool for physiological and nutritional studies including, for example, pollution monitoring.

A common and debilitating problem with this standard design is the accumulation of the cultured organism or cell on the internal filter walls of the growth chamber. This accumulation of biomass interferes with uniform inflow and outflow of the nutrient medium. To prevent such accumulation and the clogging of the growth chamber which inevitably results, the prior art has used rotating filters and intense agitation near the filter membranes. In a more recent approach to keeping the membranes clean, described in Skipnes et al., (1980) Appl. Environ. Microbiol. 40:3180325, a reversible nutrient supply pump is used to periodically reverse the direction of nutrient flow through the growth chamber of the turbidostat.

The former solutions to this problem involve complicated designs and may cause damage to the organisms or cells being cultivated thereby altering the results obtained. The latter approach undesirably introduces a significant fraction of spent nutrient medium back into the culture vessel thereby altering the basic nature of the culture process and significantly complicating the analysis of the overall results obtained.

It is an object of the present invention to provide an improved apparatus for examining the population dynamics of a colony of cells or microorganisms as a function of nutrient medium composition.

It is another object of the present invention to provide an improved cage-culture turbidostat design which substantially prevents the accumulation of microorganisms or cells on the filter membrane of the growth chamber.

It is yet another object of the present invention to provide a cage-culture turbidostat design and method of operation which avoids the problems introduced by the prior art solutions to the membrane clogging problem.

SUMMARY OF THE INVENTION

These and other objects which will be apparent to those skilled in this art are achieved by the present invention which provides an improved cage-culture turbidostat device wherein organisms are continuously cultured at a substantially constant population, said device having (i) a growth chamber with filters for keeping said organisms confined therein, (ii) pumping means for pumping fresh nutrient medium to said growth chamber, (iii) first and second conduit means for alternatively feeding said fresh nutrient medium into said growth chamber and for alternatively discharging spent nutrient medium from said growth chamber through said filters, (iv) dilution means for reducing the quantity of organisms in said growth chamber in response to a measured characteristic of said culture, and (v) valve means for directing the flow of said fresh nutrient medium into said growth chamber alternatively through said first and then said second conduit means and simultaneously directing the flow of said spend nutrient medium from said growth chamber through said second conduit means when fresh nutrient medium is flowing through said first conduit means, and through said first conduit means when fresh nutrient medium is flowing through said second conduit means, said valve means positioned in a flow path between said pumping means and said first and second conduit means.

DETAILED DESCRIPTION

The present invention is directed to an improved cage-culture turbidostat particularly useful for culturing organisms continuously at or near their maximum specific growth rate. In the turbidostat, the organism concentration is controlled directly—not the dilution rate. Consequently, if all components of the nutrient medium are present in sufficient excess, a cage-culture turbidostat may be operated over a wide range of organism concentrations while still maintaining virtually the maximum growth rate of the organism.

As used throughout the specification and claims, the term "organism" broadly encompasses both microorganisms and the cells of higher organisms. The organisms may be derived without limitation from such diverse sources as bacteria, fungi, algae, yeast, animal cells (tissue cells), e.g., from mammals, insects and fish, and plant cells. The terms "organism" and "cell" will be used interchangably throughout the specification and claims. The invention is specifically directed to the culture of organisms that require at least periodic exposure to a light source to maintain their viability.

Figure 1:
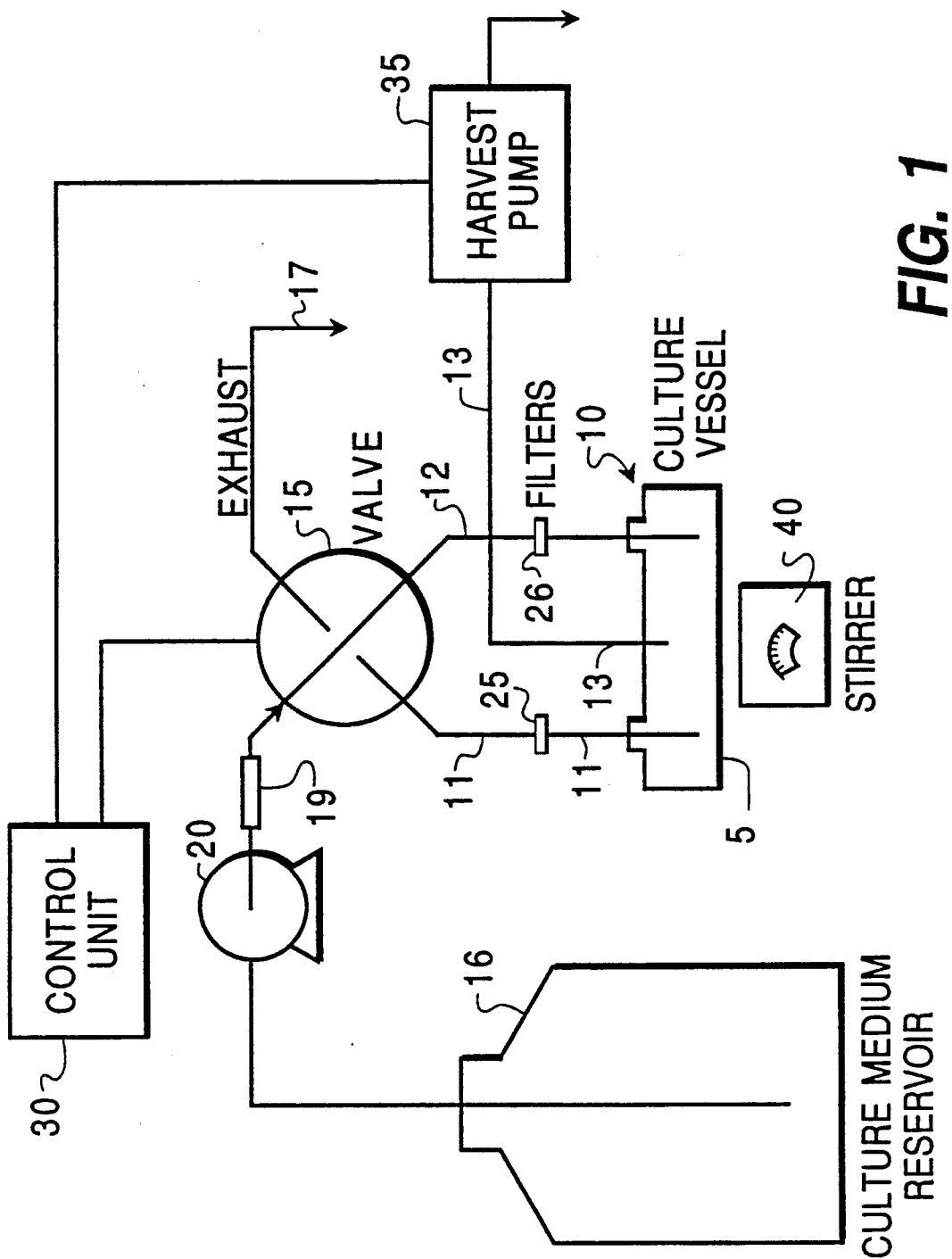
FIG. 1 is a schematic of one embodiment of the cage-culture turbidostat of the present invention having a single valve for alternatively directing the flow of fresh and spent nutrient medium through said first and second conduits.

Referring first to FIG. 1, an aqueous suspension of an organism to be studied is isolated in the growth chamber 5 of a culture vessel 10. In the broad practice of this invention, the specific design of the culture vessel is not critical although designs which lend themselves to easy sterilization are preferred. The culture vessel can vary widely in size. For example, for pollution monitoring or laboratory physiological experimentation, a volume of 2 to 4 deciliters is convenient; while for mass culture of organisms such as algae, sizes up to a thousand or more liters may be employed. The culture vessel 10 is provided with first and second conduits 11 and 12, for feeding fresh nutrient medium into the growth chamber of the culture vessel and for discharging spent nutrient medium from the growth chamber of the culture vessel. In-line filters 25 and 26 are situated in conduits 11 and 12 so as to prevent the ingress of undesirable organisms into the culture vessel and the loss of the cultured organism therefrom.

The culture vessel also is provided with a dilution or harvest conduit 13. The population of organisms in the culture vessel is controlled by harvest pump 35 which in turn is regulated automatically by control unit 30. Together, dilution or harvest conduit 13 and harvest pump 35 comprise the dilution means for the FIG. 1 cage-culture turbidostat.

Valve means 15 connects or couples the first and second conduit means 11 and 12 with both reservoir 16, containing fresh culture medium, and exhaust or waste conduit 17. In this embodiment, valve means 15 is a commercially available, rotatable four port valve of a design recognized by those skilled in this art. A suitable valve is identified in the 1985 Mandel Scientific Company catalogue as Hamilton valve, item 86729. The valve is mounted on valve drive item 86430 found in the same catalogue. Other suitable valves and sources therefore will be recognized by those skilled in this art.

Culture medium is supplied continuously to the culture vessel from the culture medium reservoir 16 by pump 20. To prevent organisms from attaching to, growing on and eventually blocking the flow of fresh and spent nutrient medium through filters 25 and 26, flow reversing valve 15 is positioned in a flow path between pump 20 and the first and second conduit means 11 and 12 and thus culture vessel 10.

Positioning valve means 15 between pump 20 and the culture vessel 10 permits the delivery lines (conduits 11 and 12) to be kept quite short. Thus, the volume of spent nutrient medium which is reintroduced into the growth chamber when the flow direction is reversed is kept to a minor portion of both the total volume of the growth chamber 5 and of the quantity of the fresh nutrient medium delivered to the growth chamber in any particular pumping cycle. Consequently, when the flow through the culture vessel 10 is reversed, the conditions within the growth chamber of the culture vessel are altered only slightly. This operation represents a substantial improvement relative to the prior art system which relies on pump 20 to provide flow reversal through the culture vessel 10.

Valve 15 alternatively directs the flow of fresh nutrient medium between conduits 11 and 12 and thus periodically reverses the flow of medium through filters 25 and 26. The reversal of valve 15 between these two positions is regulated automatically by control unit 30. When valve 15 is positioned as shown in FIG. 1, fresh nutrient medium is pumped from culture medium reservoir 16 through conduit 19 and conduit 12 into the culture vessel 10, while spent culture medium passes through conduit 11 and valve 15 into the exhaust or waste conduit 17.

Generally the growth chamber also contains some mechanism for agitating its contents, in this case stirrer 40. Agitation is needed to keep non-motile organisms in suspension and prevent nutrient gradients from developing in the chamber. Mixing also insures that the organisms are all in essentially the same physiological state. Although not shown, the culture vessel may also include an arrangment for aerating the organism suspension. Suitable designs will be apparent to those skilled in this art. Alternatively, it may be possible in some instances to simply aerate the nutrient medium before it is fed to the growth chamber.

In the operation of the FIG. 1 device, the organism population in culture vessel 10 is continuously monitored, for example, by measuring the culture's turbidity or the culture's pH, by monitoring the carbon dioxide concentration of respiration off-gases from the culture or by measuring any other characteristic of the culture which is indicative of the population in the suspension of organisms. When the measured value indicates that the population in culture vessel 10 has risen above the desired level, the control unit 30 activates harvest pump 35 causing a reduction or dilution of the organism population in culture vessel 10.

Another key feature of the FIG. 1 design is that the filters 25 and 26 used to isolate the growth chamber 5 of the culture vessel 10 are positioned in the delivery conduits to the growth chamber, i.e., the filters are located in first and second conduits 11 and 12. By positioning the filters in this fashion, filter changes are significantly facilitated. Furthermore, filters with a relatively small cross-sectional area relative to the volume of the culture vessel can be used without requiring exotic and complex designs for the culture vessel. In fact, filter area to culture vessel volume ratios of less than 10% of the prior art turbidostat designs can easily be attained with this arrangement. In the prior art design, the filter generally was part of the culture vessel itself. Thus, to avoid complex designs the area of the filter was equivalent to the cross-sectional area of the culture vessel.

By substantially reducing the filter area, the rate of flow of medium through the filters is increased and thus the likelihood of organism growth on the filters is further reduced. Furthermore, this design also relaxes filter-related design constraints on the growth chamber since the filters are no longer an integral part of the growth chamber's construction.

Figure 2:
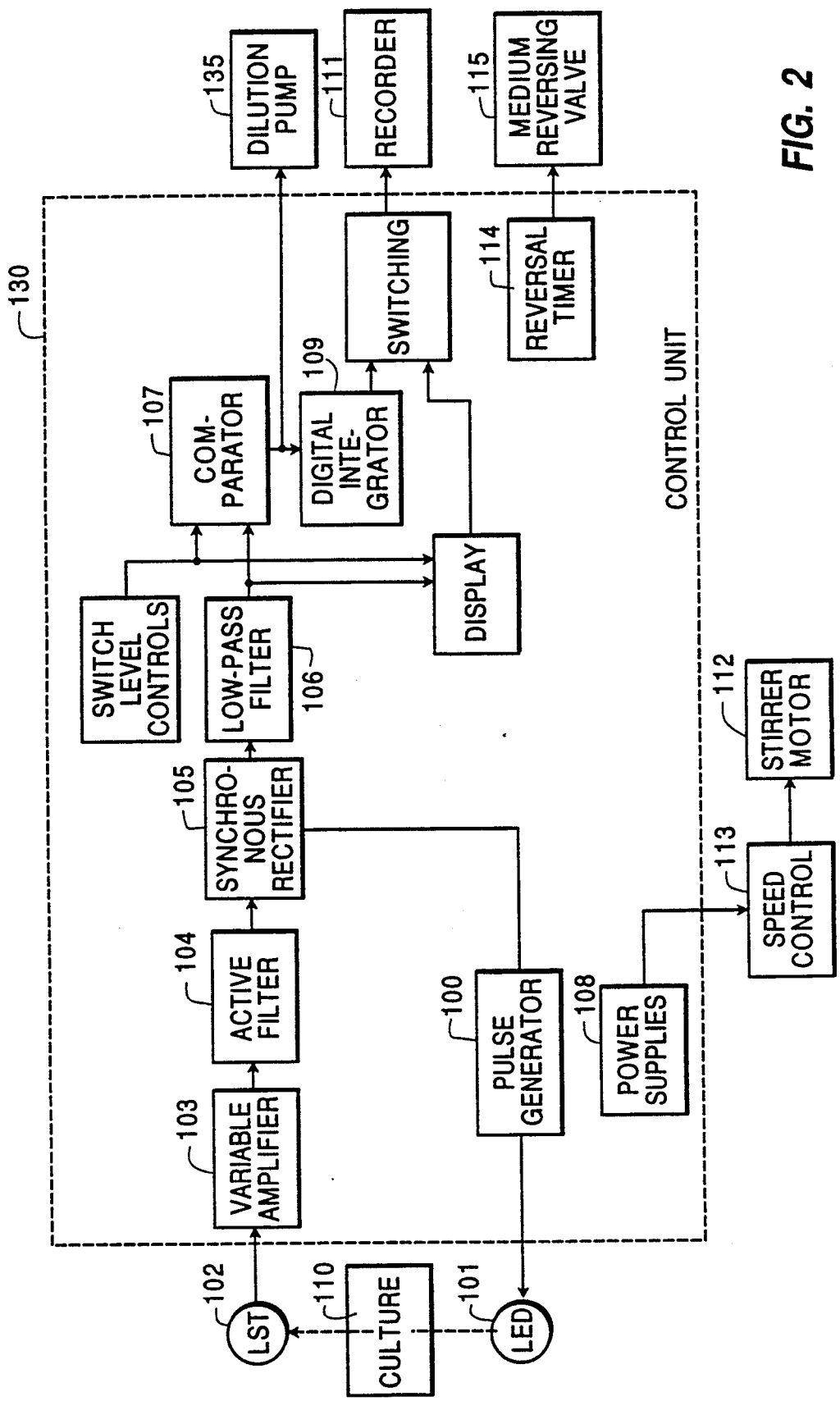
FIG. 2 is a schematic of a control unit suitable for operating the turbidostat of FIG. 1, including the function of maintaining a constant population in the growth chamber of the cage-culture turbidostat.

A suitable control unit 130 for operating the FIG. 1 cage-culture turbidostat design is illustrated in FIG. 2. In the control unit, a pulse generator 100 delivers square-pulsed light from light emitting diode 101 which passes through the growth chamber of the culture vessel 110. Transmitted light is detected by a light sensitive transistor 102, the signal is amplified by variable amplifier 103 and noise is removed by the synchronous rectifier 105 and active filter 104. After passing through the low-pass filter 106, the signal is compared with a pre-set voltage by a comparator 107. When this signal falls below the pre-set value, the dilution or harvest pump 135 is actuated and the population of organisms in the culture vessel 110 is reduced. Digital integrator 109 sums the length of time that the dilution system is operated, and this information is memorialized by the recorder 111.

The control unit also supplies the power 108 for agitating the contents of culture vessel 110 including a magnetic stirrer having stirrer motor 112 and speed control 113. Finally, the control unit controls the operation of the flow control or reversing valve 115 used to alternate the flow of fresh nutrient medium through the first and second conduits 11 and 12 in the FIG. 1 embodiment via reversal timer 114.

As noted, the present invention broadly includes all methods for effectively holding an organism population density constant in a caged culture and is not limited only to the measurement of turbidity using suitable light sensors. Included within such controls are pH and carbon dioxide measurement techniques well recognized by those skilled in this art. When pH is used to maintain a constant organism population in the growth chamber, the concentration of organisms in the growth chamber is controlled through the buffering capacity of the nutrient medium or by the difference between the initial pH of the nutrient medium and the pre-set control value for the culture vessel. In aerobic systems, a carbon dioxide analyzer can be used as the monitor for controlling organism population in the growth chamber. The rate of carbon dioxide production by a growing culture is proportional to the culture's population density. Thus, by regulating the flow of oxygenation gas to the culture vessel and accurately measuring the carbon dioxide concentration of the effluent respiration gas, it is possible to regulate the rate of dilution. Obviously, other characteristics of the caged culture, such as the production of various metabolites and products, may be monitored and used to regulate the organism population. The means for controlling the population density of the culture organism is actuated whenever the organism concentration increases above a pre-set value. As organisms are removed from the vessel either by positive dilution or by washout, the population begins to fall. Once the population density drops below the pre-set value, dilution is terminated.

Figure 3:
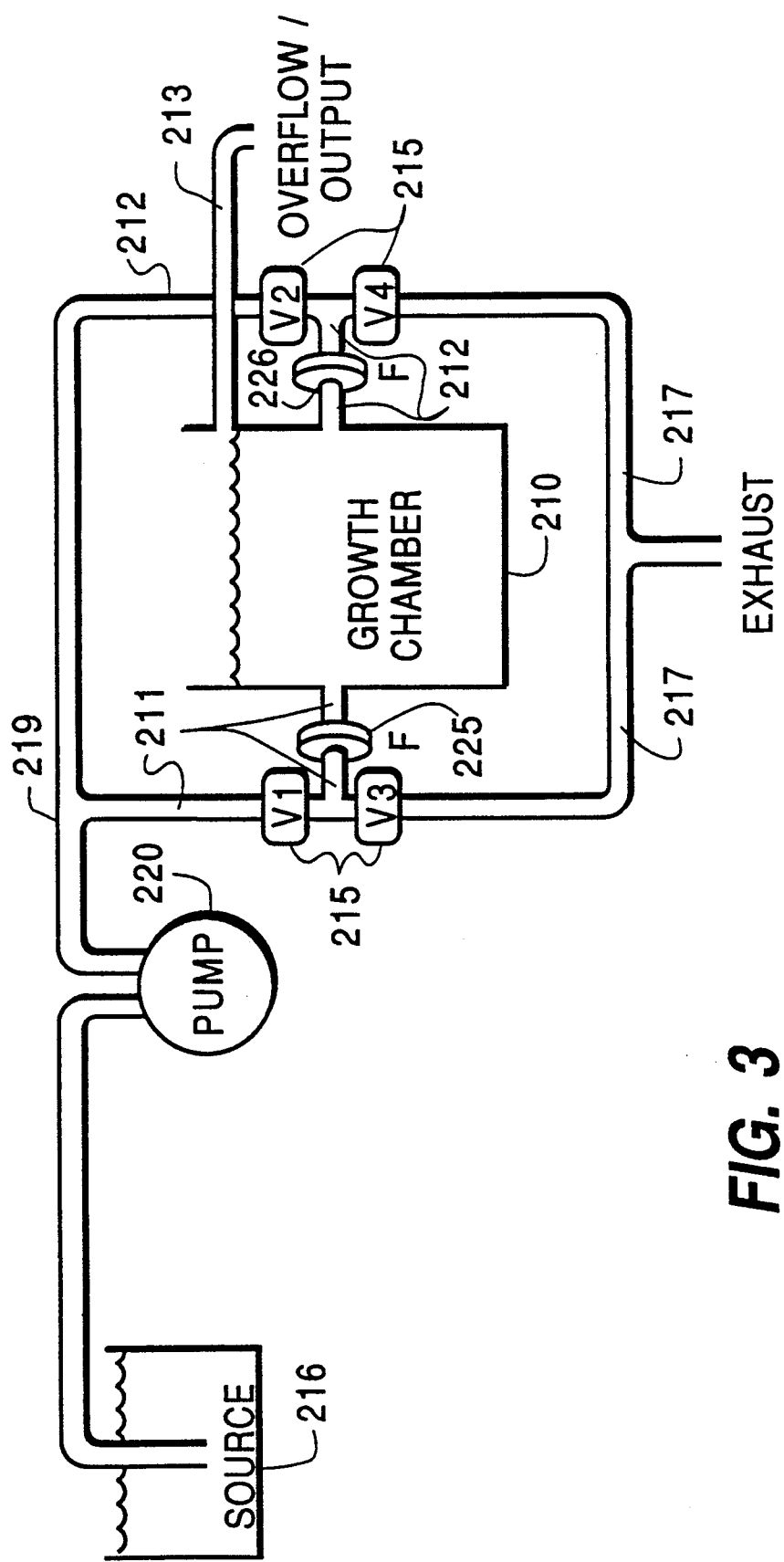
FIG. 3 is an alternative valve arrangement for directing the flow of fresh and spent nutrient medium alternatively through said first and second conduit means and for regulating the harvesting of organisms during dilution of the caged culture.

An alternate embodiment of the present invention is illustrated in FIG. 3. In this design, simple relay-tripped valves are operated in a manner which alternates the flow of fresh nutrient medium into the growth chamber through first and second conduits 211 and 212. In the operation of the FIG. 3 design, fresh nutrient medium is continuously delivered from nutrient source 216 through feedpump 220 into the feed conduit system 219. Valve means 215 which couples the first and second conduits 211 and 212 with both reservoir 216 and the exhaust or waste conduit 217 comprises valves $V_1$, $V_2$, $V_3$ and $V_4$.

In the first cycle of operation valves V1 and V4 are opened while valves V3 and V2 are closed. Consequently, fresh nutrient medium flows through valve V1, first conduit 211 and in-line filter 225 into the growth chamber of culture vessel 210. Spent nutrient medium simultaneously flows through in-line filter 226, second conduit 212 and valve V4 out through the exhaust conduit 217. In the second cycle of operation, valve V1 is closed and valve V3 is opened while valve V2 is opened and valve V4 is closed. Thus, fresh nutrient medium flows through valve V2, second conduit 212 and in-line filter 226 into the growth chamber of culture vessel 210. Spent nutrient medium simultaneously flows through in-line filter 225 and first conduit 211 and is exhausted through valve V3 and the exhaust conduit 217.

In this embodiment, instead of using a dilution or harvest pump to control the organism population, fresh nutrient medium is used for this purpose. For example, consider the case where fresh nutrient is being pumped through valve V1 and spent nutrient medium is being exhausted through valve V4 and the control unit indicates that the organism population in culture vessel 210 has increased above the pre-set value. Dilution is therefore necessary, and is accomplished by closing valve V4, causing organisms to be displaced through the overflow or dilution conduit 213. In the event, dilution is required when fresh nutrient medium is flowing through valve V2 and spent nutrient medium is flowing through valve V3, valve V3 is closed, causing excess organisms to overflow into dilution conduit 213.

As in the FIG. 1 embodiment, by using valve means 215 to alternate the direction of flow of fresh nutrient medium through the growth chamber of the culture vessel and thus through the filters defining growth chamber of the culture vessel, it is possible to avoid the accumulation of organisms on the filters and also significantly minimize the re-introduction of spent nutrient medium into the growth chamber. As clearly shown in FIG. 3, the only spent nutrient medium that is re-introduced into the growth chamber is that residing in the first and second conduits between the culture vessel 210 and valves V1 and V3 or V2 and V4 respectively. FIG. 3 illustrates that this volume can be kept at a minimum.

In the only other cage-culture turbidostat reported in the literature, clogging of the membranes which define the growth chamber of the device is prevented by reversing the flow direction of the pump which feeds fresh nutrient medium into the culture vessel. This design, however, results in a significant volume of spent nutrient medium being pumped back through the growth chamber, thus potentially decreasing the normal rate of development of the caged organisms. In fact, spent medium also is potentially pumped back into the nutrient supply vessel. Thus, there is a significant likelihood that the concentration of the fresh nutrient medium itself is steadily altered. Such operation makes any calculations regarding nutrient availability or nutrient stress extremely difficult, if not impossible, and also places any estimates of the effective concentration of added toxicants in significant doubt.

The cage-culture turbidostat of this invention can maintain a constant organism population under nutrient loadings which vary from far in excess of that needed for the highest growth rates possible under a given set of conditions of temperature and illumination, to a nutrient loading which just supports replacement of lost organisms. Similarly, the cage-culture turbidostat of this invention can hold a population of organisms at a constant growth rate for very long periods of time. Thus, the system is particularly well adapted to physiological and nutritional studies of planktonic organisms, especially phytoplankton and bacterioplankton. When coupled with a suitable indicator organism, the ease in holding a population or organisms at a constant growth rate and constant population density, and of recording instantaneously any deviation from either, makes the present invention an excellent pollution monitor.

The invention can serve as a well-controlled continuous cultivator for mass growth of organisms including planktonic species. The proper conditions for growth at the required population density and growth rate can be determined in laboratory-sized units, and then placed into effect in a mass-culture analogue. The ability of the apparatus of this invention to maintain known growth rates and known population densities, and thus known harvest rates, makes possible the use of organisms as feedstock for continuous processes, such as in the feeding of invertebrates and invertebrate larvae or as in the separation and purification of specialty chemicals or pharmaceuticals.

While specific embodiments of the present invention had been described herein, it will be recognized that various modifications thereof will occur to those skilled in the art. Therefore, the scope of the invention is limited solely by the scope of the appended claims.

We claim:

1. In a cage-culture turbidostat device wherein organisms are continuously cultured at a substantially constant population comprising a growth chamber having filters for keeping said organisms confined therein; pumping means for pumping fresh nutrient medium to said growth chamber; a first conduit for feeding fresh nutrient medium into said growth chamber, a second conduit for discharging spent nutrient medium from said growth chamber, means for monitoring the organism population density in said growth chamber by measuring turbidity and dilution means for reducing the quantity of organisms in said growth chamber, the improvement which comprises valve means for directing the flow of said fresh nutrient medium into said growth chamber alternatively through said first conduit and then said second conduit, said filters being positioned in said first and second conduits, said valve means simultaneously directing the flow of said spent nutrient medium from said growth chamber through said second conduit while fresh nutrient medium is flowing through said first conduit, and through said first conduit while fresh nutrient medium is flowing through said second conduit, said valve means being positioned in a flow path between said pumping means and said growth chamber, said first and second conduit having a substantially minor cross-sectional area relative to the cross-sectional area of the growth chamber to define a minor volume relative to the growth chamber, said minor volume being defined by a distance between the valve means and said filters, to limit reintroduction of any spent nutrient medium into the growth chamber upon flow reversal of said fresh nutrient medium to a minor portion, by volume, of the growth chamber.

2. The device of claim 1 wherein the dilution means includes a dilution pump and a control unit for actuating said dilution pump in response to the turbidity of said culture medium in said growth chamber.

3. The device of claim 2 wherein said means for monitoring population density by measuring turbidity comprises a combination of a light emitting diode and a light sensitive transistor.

4. The device of claim 1 wherein a control unit automatically controls said valve means.

* * * * *